United States Patent [19]

Thiele

[11] 4,263,038
[45] Apr. 21, 1981

[54] SYNERGISTIC HERBICIDAL COMPOSITIONS

[75] Inventor: Gerald H. Thiele, Sunnyvale, Calif.

[73] Assignee: Stauffer Chemical Company, Westport, Conn.

[21] Appl. No.: 125,815

[22] Filed: Feb. 29, 1980

Related U.S. Application Data

[63] Continuation-in-part of Ser. No. 80,874, Oct. 1, 1979, abandoned.

[51] Int. Cl.³ .............................................. A01N 43/64
[52] U.S. Cl. .............................................. 71/92; 71/76
[58] Field of Search .............................. 71/92, 95, 76

[56] References Cited

U.S. PATENT DOCUMENTS 2,670,282  2/1954  Allen ........................................ 71/92
4,110,105  8/1978  Teach ....................................... 71/95

OTHER PUBLICATIONS

Klingman et al., Weed Science, Principles and Practice, (John Wiley & Sons, New York, 1975), pp. 89–95.

Primary Examiner—Alton D. Rollins
Attorney, Agent, or Firm—M. Henry Heines; Veronica Devitt

[57] ABSTRACT

Synergistic herbicidal activity is displayed by a composition comprising the following two components:
(a) a pyrrolidone of the formula

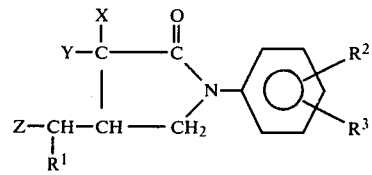

in which X is selected from the group consisting of hydrogen, chlorine, and methyl; Y is selected from the group consisting of hydrogen, chlorine, and bromine; Z is selected from the group consisting of chlorine and bromine; $R^1$ is selected from the group consisting of hydrogen and $C_1$–$C_4$ alkyl; $R^2$ is selected from the group consisting of hydrogen, $C_1$–$C_4$ alkyl, acetyl, trifluoromethyl, nitro, cyano, $C_1$–$C_4$ alkoxy, $C_1$–$C_4$ alkylthio, $C_1$–$C_4$ alkylsulfonyl, $C_1$–$C_4$ alkylsulfinyl, trifluoromethylthio, trifluoromethylsulfinyl, trifluoromethylsulfonyl, pentafluoropropionamido, and 3-methylureido; and $R^3$ is selected from the group consisting of hydrogen, $C_1$–$C_4$ alkyl, chlorine and trifluoromethyl; and
(b) 3-amino-1,2,4-triazole, at a weight ratio of (a) to (b) of from about 0.01:1 to about 20:1.

6 Claims, No Drawings

SYNERGISTIC HERBICIDAL COMPOSITIONS

CROSS REFERENCE TO RELATED APPLICATIONS

This is a continuation-in-part of application Ser. No. 080,874, filed Oct. 1, 1979, now abandoned.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, active herbicides have been shown to be more effective in combination than when applied individually. The result is often term "synergism," since the combination demonstrates a potency or activity level exceeding that which it would be expected to have, based on a knowledge of the individual potencies of the components. The present invention resides in the discovery that 3-amino-1,2,4-triazole and certain pyrrolidones, already known individually for their herbicidal potency, display this synergistic effect when applied in combination.

PRIOR ART

The two classes of compounds forming the combination which is the subject of the present invention are independently known in the art for their effects on plant growth. Pyrrolidones are disclosed as herbicides in U.S. Pat. No. 4,110,105 (Teach, Aug. 29, 1979), and 3-amino-1,2,4-triazole is disclosed as a plant growth regulator in U.S. Pat. No. 2,670,282 (Allen, Feb. 23, 1954).

DESCRIPTION OF THE INVENTION

It has now been discovered that synergism in the control of undesirable vegetation is exhibited by compositions comprising a mixture of the following two components:

(a) a pyrrolidone of the formula

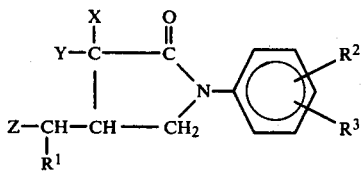

in which

X is selected from the group consisting of hydrogen, chlorine and methyl;

Y is selected from the group consisting of hydrogen, chlorine and bromine;

Z is selected from the group consisting of chlorine and $C_1$-$C_4$ alkyl;

$R^1$ is selected from the group consisting of hydrogen and $C_1$-$C_4$ alkyl;

$R^2$ is selected from the group consisting of hydrogen, halogen, $C_1$-$C_4$ alkyl, acetyl, trifluoromethyl, nitro, cyano, $C_1$-$C_4$ alkoxy, $C_1$-$C_4$ alkylthio, $C_1$-$C_4$ alkylsulfinyl, $C_1$-$C_4$ alkylsulfonyl, trifluoromethylthio, trifluoromethylsulfinyl, trifluoromethylsulfonyl, pentafluoropropionamido, and 3-methylureido; and $R^3$ is selected from the group consisting of hydrogen, $C_1$-$C_4$ alkyl, chlorine and trifluoromethyl; and (b) 3-amino-1,2,4-triazole, which has the following formula

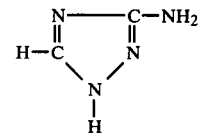

The terms "alkyl," "alkoxy," "alkylthio," etc., as used herein include both straight-chain and branched-chain groups. All carbon atom ranges are inclusive of upper and lower limits.

Examples of pyrrolidones useful in the present invention are:

1-phenyl-3-chloro-4-chloromethyl-2-pyrrolidone
1-phenyl-3,3-dichloro-4-chloromethyl-2-pyrrolidone
1-(2',6'-dimethylphenyl)-3-chloro-4-chloromethyl-2-pyrrolidone
1-m-chlorophenyl-3-chloro-4-chloromethyl-2-pyrrolidone
1-p-chlorophenyl-3-chloro-4-chloromethyl-2-pyrrolidone
1-m-trifluoromethylphenyl-3-chloro-4-chloromethyl-2-pyrrolidone
1-phenyl-3-chloro-3-methyl-4-chloromethyl-2-pyrrolidone
1-(3',4'-dichlorophenyl)-3,3-dichloro-4-chloromethyl-2-pyrrolidone
1-m-trifluoromethylphenyl-3,3-dichloro-4-chloromethyl-2-pyrrolidone
1-m-trifluoromethylphenyl-3-chloro-4-methyl-4-chloromethyl-2-pyrrolidone
1-p-tolyl-3-chloro-4-chloromethyl-2-pyrrolidone
1-m-fluorophenyl-3-chloro-4-chloromethyl-2-pyrrolidone
1-m-trifluoromethyl-3-bromo-4-bromomethyl-2-pyrrolidone
1-(3',4'-dichlorophenyl)-3-chloro-4-chloromethyl-2-pyrrolidone
1-m-pentafluoropropionamidophenyl-3-chloro-4-chloromethyl-2-pyrrolidone
cis-1-m-trifluoromethylphenyl-3-chloro-4-chloromethyl-2-pyrrolidone
trans-1-m-trifluoromethylphenyl-3-chloro-4-chloromethyl-2-pyrrolidone
1-m-nitrophenyl-3-chloro-4-chloromethyl-2-pyrroiidone
1-(3',5'-dichlorophenyl)-3-chloro-4-chloromethyl-2-pyrrolidone
1-m-trifluoromethylphenyl-3-chloro-4-(1'-chloroethyl)-2-pyrrolidone
1-m-cyanophenyl-3-chloro-4-chloromethyl-2-pyrrolidone
1-(3',5'-dichlorophenyl)-3,3-dichloro-4-chloromethyl-2-pyrrolidone
1-m-trifluoromethylphenyl-3,3-dichloro-4-(1'-chloroethyl)-2-pyrrolidone
1-m-cyanophenyl-3,3-dichloro-4-chloromethyl-2-pyrrolidone
1-(3'-trifluoromethyl-4'-chlorophenyl)-3-chloro-4-chloromethyl-2-pyrrolidone 1-(3'-trifluoromethyl-4'-chlorophenyl)-3,3-dichloro-4-chloromethyl-2-pyrrolidone 1-m-trifluoromethylthiophenyl-3-chloro-4-chloromethyl-2-pyrrolidone 1-m-methylthiophenyl-3-chloro-4-chloromethyl-2-pyrrolidone 1-m-trifluoromethylsulfinylphenyl-3-chloro-4-chloromethyl-2-pyrrolidone 1-m-methylsulfinylphenyl-3-chloro-4-chloromethyl-2-pyrrolidone 1-m-methylsulfonylphenyl-3-chloro-4-chloromethyl-2-pyrrolidone 1-m-trifluoromethylsulfonylphenyl-3-chloro-4-chloromethyl-2-pyrrolidone 1-(3',5'-bis-trifluoromethylphenyl)-3-chloro-4-chloromethyl-2-pyrrolidone 1-m-methoxyphenyl-3-chloro-4-chloromethyl-2-pyrrolidone 1-m-acetylphenyl-3-chloro-4-chloromethyl-2-pyrrolidone 1-m-tolyl-3-chloro-4-chloromethyl-2-pyrrolidone 1-m-trifluoromethylphenyl-4-chloromethyl-2-pyrrolidone 1-m-bromophenyl-3-chloro-4-chloromethyl-2-pyrrolidone 1-o-chlorophenyl-3-chloro-4-chloromethyl-2-pyrrolidone 1-m-iodophenyl-3-chloro-4-chloromethyl-2-pyrrolidone 1-p-methoxyphenyl-3-chloro-4-chloromethyl-2-pyrrolidone 1-o-trifluoromethylphenyl-3-chloro-4-chloromethyl-2-pyrrolidone These and other pyrrolidones within the scope of the invention can be prepared by the procedures described in U.S. Pat. No. 4,110,105.

In the compositions of the present invention, pyrrolidones of the following formula are preferred:

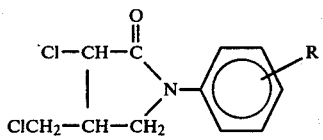

in which R is cyano or trifluoromethyl.

The terms "synergism" and "synergistic" are used herein to convey the result observed when a combination of herbicides demonstrates a potency in excess of that which the combination would be expected to produce on the basis of the potencies of each herbicide applied individually.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example: killing, retardation, stimulating, leaf burn, dwarfing and the like. The term "plants" is used to include germinating seeds, emerging seedlings and established vegetation, including roots and aboveground portions.

In the compositions of this invention, the pyrrolidone:triazole weight ratio at which the herbicidal response is synergistic lies within the range of about 0.01:1 to about 20:1, preferably about 0.1:1 to about 10:1, most preferably about 0.1:1 to about 5:1.

Application rates will depend upon the weeds to be controlled and the degree of control desired. In general, the compositions of this invention are most efficiently employed at a rate of 0.01 to 50 pounds per acre (0.011 to 56 kilograms per hectare) of the active ingredients, preferably 0.1 to 25 pounds per acre (0.11 to 28 kilograms per hectare).

The following examples provide further illustrations demonstrating the synergistic herbicidal response of the present compositions.

EXAMPLE I

This example demonstrates the synergistic response of 1-m-trifluoromethylphenyl-3-chloro-4-chloromethyl-2-pyrrolidone and 3-amino-1,2,4-triazole in combined post-emergence application to a variety of weeds.

Fiber flats measuring 13.3×18.5×6.4 cm were filled to a depth of 5.0 cm with loamy sand soil, containing 50 parts per million (ppm) each of the commercial fungicide cis-N[(trichloromethyl)thio]-4-cyclohexene-1,2-dicarboximide (Captan ®) and 18-18-18 fertilizer (percentages of $N-P_2O_5-K_2O$ on a weight basis). Several rows were impressed across the width of each flat and each row was seeded with a single weed species. The weed species included johnsongrass (*Sorghum halepense*), annual ryegrass (*Lolium multiflorum*), annual morning glory (*Ipomoea purpurea*), wild oat (*Avena fatua*), jimsonweed (*Datura stramonium*), and velvetleaf (*Abutilon theophrasti*). Ample seeds were planted to give about 20 to 50 seedlings per row after emergence depending on the size of the plants. The flats were then placed in a greenhouse for two weeks, where they were watered regularly.

At the end of this period, the foliage on the emergent weeds was sprayed with aqueous solutions of the test compounds. The quantities sprayed were such that the amount of each test compound applied per flat corresponded to the desired application rate in pounds per acre. In control flats, the test compounds were applied alone at various application rates, whereas in the test flats, solutions containing both compounds were applied. Additional flats not treated at all were used as standards for measuring the extent of weed control occurring in the treated flats.

Eighteen days after treatment, the control and test flats were compared to the standards and each row was rated visually in terms of percent control ranging from 0% to 100%, with 0% representing the same degree of growth as the same row in the standard and 100% representing complete kill of all weeds in the row. All types of plant injury were taken into consideration.

The results of these tests are listed in Table I in the columns headed by the symbol "O" (indicating the "observed" results), each figure representing the average of two replications of the same test. These results are compared with the expected results, shown in the columns headed by the symbol "E," derived from the control data using Limpel's formula (Limpel et al., 1962, "Weed Control by Dimethylchloroterephthalate Alone and in Certain Combinations," *Proc. NEWCC.*, Vol. 16, pp. 48-53):

$$E = X + Y - XY/100$$

where

X = observed percent injury when one of the herbicides is used alone, and
Y = observed percent injury when the other herbicide is used alone.

An asterisk (*) is used to indicate the tests where the results show synergism, i.e., where the observed result exceeds the expected result. It is clear from the table that synergism was observed at many of the application rates tested.

TABLE I

HERBICIDE SYNERGISM TEST RESULTS

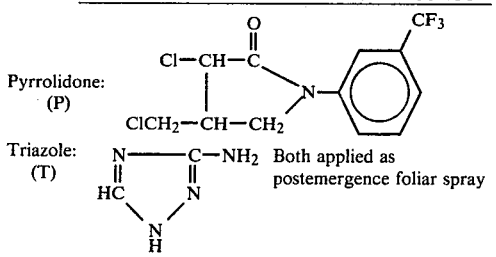

Pyrrolidone: (P)

Triazole: (T) Both applied as postemergence foliar spray

| Application Rate (lb/A) | | Percent Control - O:Observed E:Expected | | | | | | | | | | |
|---|---|---|---|---|---|---|---|---|---|---|---|---|
| | | Johnson-grass | | Rye-grass | | Morning glory | | Wild Oat | | Jimson-weed | | Velvet-leaf |
| P | T | O | E | O | E | O | E | O | E | O | E | O E |
| Control Data: | | | | | | | | | | | | |
| 0.125 | — | 0 | | 0 | | 0 | | 0 | | 85 | | 70 |
| 0.25 | — | 0 | | 0 | | 0 | | 0 | | 58 | | 73 |
| 0.5 | — | 30 | | 0 | | 0 | | 40 | | 100 | | 83 |
| — | 0.025 | 35 | | 0 | | 0 | | 0 | | 95 | | 85 |
| — | 0.033 | 30 | | 0 | | 0 | | 0 | | 83 | | 85 |
| — | 0.05 | 63 | | 0 | | 0 | | 0 | | 80 | | 98 |
| Test Data: | | | | | | | | | | | | |
| 0.125 | 0.025 | 85* | 35 | 0 | 0 | 10* | 0 | 0 | 0 | 25 | 99 | 80 96 |
| 0.125 | 0.033 | 75* | 30 | 30* | 0 | 30* | 0 | 0 | 0 | 35 | 97 | |
| 0.125 | 0.05 | 83* | 63 | 40* | 0 | 40* | 0 | 0 | 0 | | | |
| 0.25 | 0.025 | 75* | 35 | 15* | 0 | 10* | 0 | 15* | 0 | 58 | 98 | |

TABLE I-continued

HERBICIDE SYNERGISM TEST RESULTS

Pyrrolidone: (P)

Triazole: (T) Both applied as postemergence foliar spray

| Application Rate (lb/A) | | Percent Control - O:Observed E:Expected | | | | | | | | | | |
|---|---|---|---|---|---|---|---|---|---|---|---|---|
| | | Johnson-grass | | Rye-grass | | Morning glory | | Wild Oat | | Jimson-weed | | Velvet-leaf |
| P | T | O | E | O | E | O | E | O | E | O | E | O E |
| 0.25 | 0.033 | 85* | 30 | 23* | 0 | 15* | 0 | 40* | 0 | 70 | 93 | |
| 0.25 | 0.05 | 80* | 63 | 30* | 0 | 40* | 0 | 50* | 0 | 65 | 92 | |
| 0.5 | 0.025 | 98* | 55 | 45* | 0 | 68* | 0 | 65* | 40 | | | |
| 0.5 | 0.033 | 84* | 51 | 45* | 0 | 80* | 0 | 100* | 40 | | | |
| 0.5 | 0.05 | 79* | 74 | 73* | 0 | 63* | 0 | 100* | 40 | | | |

*Synergistic effect shown.
·Blank spaces indicate 100% control in both observed and expected results, precluding evaluation of synergism.

EXAMPLE II

This example demonstrates the synergistic response of the same herbicides used in Example I at higher application rates. Similar fiber flats were used, and the weed species included johnsongrass, wild oat, annual ryegrass, and annual morning glory as in Example I, plus yellow nutsedge (Cyperus esculentus). The weed foliage was sprayed with the test solutions three weeks after the seeds were planted, and injury ratings were taken four weeks later.

The results are shown in Table II, with synergism evident.

TABLE II

HERBICIDE SYNERGISM TEST RESULTS

Pyrrolidone:    Triazole:

| Application Rate (lb/A) | | Postemergence Foliar Spray Application Percent Control - O:Observed E:Expected | | | | | | | | |
|---|---|---|---|---|---|---|---|---|---|---|
| Pyrrol-idone | Triazole | Johnson-grass | | Wild Oat | | Rye-grass | | Morning-glory | | Nut-sedge |
| | | O | E | O | E | O | E | O | E | O E |
| Control Data: | | | | | | | | | | |
| 0.125 | — | 30 | | 0 | | 0 | | 0 | | 0 |
| 0.25 | — | 65 | | 0 | | 0 | | 60 | | 0 |
| 0.5 | — | 70 | | 30 | | 60 | | 98 | | 20 |
| 1.0 | — | 80 | | 100 | | 85 | | 100 | | 50 |
| — | 0.0625 | 90 | | 100 | | 98 | | 0 | | 20 |
| — | 0.125 | 90 | | 100 | | 100 | | 0 | | 75 |
| — | 0.25 | 95 | | 100 | | 100 | | 10 | | 80 |
| — | 0.5 | 95 | | 100 | | 100 | | 20 | | 98 |
| Test Data: | | | | | | | | | | |
| 0.125 | 0.0625 | 65 | 93 | | | 70 | 98 | 0 | 0 | 0 20 |
| 0.125 | 0.125 | 95* | 93 | | | | | 0 | 0 | 95* 75 |
| 0.125 | 0.25 | | | | | | | 100* | 10 | 100* 80 |
| 0.125 | 0.5 | | | | | | | 60* | 20 | |
| 0.25 | 0.0625 | | | | | | | 0 | 60 | 95* 20 |
| 0.25 | 0.125 | | | | | | | 30 | 60 | 100* 75 |
| 0.25 | 0.25 | | | | | | | 75* | 64 | 100* 80 |
| 0.25 | 0.5 | | | | | | | 100* | 68 | |

TABLE II-continued
HERBICIDE SYNERGISM TEST RESULTS

Pyrrolidone:  Triazole:

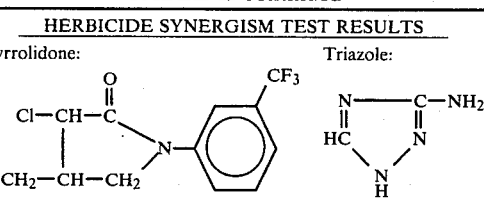

| Application Rate (lb/A) | | Postemergence Foliar Spray Application Percent Control - O:Observed E:Expected | | | | | | | | |
|---|---|---|---|---|---|---|---|---|---|---|
| Pyrrol- | | Johnson-grass | | Wild Oat | | Rye-grass | | Morning-glory | | Nut-sedge | |
| idone | Triazole | O | E | O | E | O | E | O | E | O | E |
| 0.5 | 0.0625 | | | | | | | 40 | 98 | 100* | 36 |
| 0.5 | 0.125 | | | | | | | 40 | 98 | 100* | 80 |
| 0.5 | 0.25 | | | | | | | 40 | 98 | 100* | 84 |
| 0.5 | 0.5 | | | | | | | 50 | 98 | | |
| 1.0 | 0.0625 | | | | | | | 75 | 100 | 100* | 60 |
| 1.0 | 0.125 | | | | | | | 70 | 100 | 100* | 88 |
| 1.0 | 0.25 | | | | | | | 70 | 100 | 100* | 90 |
| 1.0 | 0.5 | | | | | | | 80 | 100 | | |

*Synergistic effect shown.
Blank spaces indicate 100% control in both observed and expected results, precluding evaluation of synergism.

EXAMPLE III

This example demonstrates the synergistic herbicidal response of 1-m-cyanophenyl-3-chloro-4-chloromethyl-2-pyrrolidone and 3-amino-1,2,4-triazole in combined pre-emergence soil surface spray application. Fiber flats similar to those of Examples I and II were used, and the weed species included wild oat, yellow nutsedge, annual morning glory, and annual ryegrass as in Examples I and II, together with red oat (*Avena sativa*), and nightshade (*Cyperus sp.*). The soil was sprayed with the test solutions one day after seeding, and injury ratings were taken nineteen days later.

The results are shown in Table III, with synergism evident.

TABLE III
HERBICIDE SYNERGISM TEST RESULTS

Pyrrolidone: (P)  Triazole: (T)

| Application Rates (lb/A) | | Pre-emergence surface spray application Percent Control - O:Observed E:Expected | | | | | | | | | |
|---|---|---|---|---|---|---|---|---|---|---|---|
| P | T | Wild Oat | | Nut-sedge | | Morn-ing-glory | | Red Oat | | Rye-grass | | Night-shade | |
| | | O | E | O | E | O | E | O | E | O | E | O | E |
| Control Data: | | | | | | | | | | | | | |
| 0.0625 | — | 0 | | 0 | | 0 | | 0 | | 0 | | 0 | |
| 0.125 | — | 0 | | 0 | | 0 | | 0 | | 0 | | 0 | |
| 0.25 | — | 0 | | 0 | | 10 | | 0 | | 0 | | 30 | |
| — | 0.025 | 0 | | 0 | | 0 | | 0 | | 0 | | 0 | |
| — | 0.050 | 10 | | 0 | | 0 | | 0 | | 0 | | 40 | |
| — | 0.075 | 20 | | 0 | | 0 | | 0 | | 0 | | 60 | |
| Test Data: | | | | | | | | | | | | | |
| 0.0625 | 0.025 | 20* | 0 | 0 | 0 | 0 | 0 | 0 | 0 | 0 | 0 | 0 | 0 |
| 0.0625 | 0.050 | 20* | 10 | 0 | 0 | 0 | 0 | 0 | 0 | 0 | 0 | 30 | 40 |
| 0.0625 | 0.075 | 20 | 20 | 0 | 0 | 0 | 0 | 0 | 0 | 0 | 0 | 65* | 60 |
| 0.125 | 0.025 | 0 | 0 | 0 | 0 | 0 | 0 | 0 | 0 | 0 | 0 | 20* | 0 |
| 0.125 | 0.050 | 0 | 10 | 0 | 0 | 0 | 0 | 0 | 0 | 0 | 0 | 60* | 40 |
| 0.125 | 0.075 | 30* | 20 | 0 | 0 | 0 | 0 | 0 | 0 | 20* | 0 | 75* | 60 |
| 0.25 | 0.025 | 20* | 0 | 0 | 0 | 0 | 10 | 0 | 0 | 0 | 0 | 20 | 30 |
| 0.25 | 0.050 | 40* | 10 | 0 | 0 | 0 | 10 | 0 | 0 | 0 | 0 | 60* | 55 |
| 0.25 | 0.075 | 60* | 20 | 0 | 0 | 0 | 10 | 0 | 0 | 30* | 0 | 70 | 72 |

*Synergistic effect shown.

The compositions of this invention are useful as herbicides demonstrating synergistic activity for the control of undesirable vegetation. The compositions can be formulated in the same manner in which herbicides are generally formulated, and can be applied either separately or in combination. The compositions are applied to the locus where control is desired by any conventional method. The loci of application include soil, seeds, and seedlings, as well as established vegetation.

Formulations will generally contain one or more additives. Among these are inert ingredients and diluent carriers such as organic solvents, water, dust and granule carriers, and surface active, wetting, dispersing, and emulsifying agents. Fertilizers, such as ammonium nitrate, urea and superphosphate can also be included, as well as aids to rooting and growth, such as compost, manure, humus, sand, etc.

The most common formulations are dusts, wettable powders, granules, solutions and emulsifiable concentrates.

Dusts are free-flowing powder compositions containing the herbicidal compound impregnated on a particulate carrier. The particle size of the carrier is usually in the approximate range of 30 to 50 microns. Examples of suitable carriers are talc, bentonite, diatomaceous earth, and pyrophyllite. Anticaking and antistatic agents can be added, if desired. The composition generally contains up to 50% of active ingredient. Dusts, like liquid compositions can be applied by airplanes or ground spraying equipment.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols; salts of sulfonic acids; esters of long chain fatty acids; and polyhydric alcohols, in which the alcohol groups are free, omega-substituted polyethylene glycols of relatively long chain length.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

It is not necessary that the compositions be admixed with the soil particles. After application by the above discussed methods, they may be distributed below the soil surface to a depth of at least one-half inch by conventional means such as discing, dragging, or mixing.

What is claimed is:

1. A synergistic herbicidal composition comprising a mixture of
    (a) an effective amount of a pyrrolidone of the formula

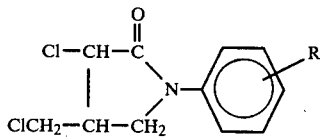

in which R is cyano or trifluoromethyl, and
    (b) an effective amount of 3-amino-1,2,4-triazole, at a weight ratio of (a) to (b) of from about 0.25:1 to about 20:1.

2. A composition according to claim 1 in which R is 3-trifluoromethyl.

3. A composition according to claim 1 in which R is 3-cyano.

4. A method of controlling undesirable vegetation which comprises applying to the locus where control is desired a herbicidal composition comprising a mixture of
    (a) an effective amount of a pyrrolidone of the formula

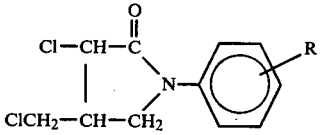

in which R is cyano or trifluoromethyl, and
    (b) an effective amount of 3-amino-1,2,4-triazole, at a weight ratio of (a) to (b) of from about 0.25:1 to about 20:1.

5. A method according to claim 4 in which R is 3-trifluoromethyl.

6. A method according to claim 4 in which R is 3-cyano.

* * * * *